United States Patent
Shahid

(10) Patent No.: US 6,525,147 B1
(45) Date of Patent: Feb. 25, 2003

(54) USE OF DIAMINES AND ALKANOLAMINES TO INHIBIT UNSATURATED MONOMER POLYMERIZATION

(75) Inventor: Muslim D. Shahid, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 28 days.

(21) Appl. No.: 09/886,528

(22) Filed: Jun. 20, 2001

(51) Int. Cl.$^7$ .................................................. C08F 2/38
(52) U.S. Cl. ............................ 526/82; 526/83; 526/84; 526/227; 526/319; 526/341; 526/303.1; 526/335; 526/346; 526/329.2
(58) Field of Search .............................. 526/82, 83, 84, 526/227, 319, 341, 303.1, 335, 346, 329.2

(56) References Cited

U.S. PATENT DOCUMENTS

| 5,527,447 A | | 6/1996 | Roof |
| 5,614,080 A | * | 3/1997 | Roof ........................... 208/48 |

OTHER PUBLICATIONS

Abstract for M. Calull, et al., "Kinetic–thermodynamic Study of Hydrogen Peroxide Decomposition in Basic Media Catalyzed by Mn(II). Influence of Several Other Ligands," Thermochemica Acta, vol. 125, No. 1, 1988, pp. 319–325.
Abstract of T. Funazukuri, et al. "Decomposition of 2–Aminoethanol in Sub–and Supercritical Water With/Without Hydrogen Peroxide," Fuel, vol. 78, No. 9, Jul. 1999, pp. 1117–1119.

\* cited by examiner

*Primary Examiner*—David W. Wu
*Assistant Examiner*—William Cheung
(74) *Attorney, Agent, or Firm*—Madan, Mossman & Sriram, P.C.

(57) ABSTRACT

It has been discovered that the polymerization of unsaturated compounds, such as butadiene, may be inhibited by the addition of a diene and/or alkanolamine inhibitor. The inhibitor is believed to catalytically destroy peroxides present, such as hydrogen peroxide, which may be present in trace amounts. Particularly useful inhibitors include, but are not limited to, ethylenediamine (EDA) and monoethanolamine (MEA).

13 Claims, No Drawings

USE OF DIAMINES AND ALKANOLAMINES TO INHIBIT UNSATURATED MONOMER POLYMERIZATION

FIELD OF THE INVENTION

The present invention relates to methods and compositions for inhibiting the polymerization of diene monomers, and more particularly relates, in one embodiment, to methods and compositions for inhibiting the polymerization of butadiene monomers by decomposing hydrogen peroxide.

BACKGROUND OF THE INVENTION

In the production of olefins, such as a diene, the so-called popcorn polymer having a porous, three-dimensional structure occurs frequently and undesirably in process apparatus due to the unintentional polymerization of the olefin. Popcorn polymerization occurs in refining and distillation of the monomer, or during recovery of the monomer after termination of intentional polymerization such as during the production of poly-butadiene and synthetic rubber, in particular styrene-butadiene rubber. Popcorn polymerization occurs both in the gaseous phase and the liquid phase. It is more likely to occur when the concentration of the olefin monomer is high and the temperature is high. Trace amounts of peroxides used to intentionally generate free radicals to initiate and perpetuate polymerization may remain in these systems to produce free radicals that cause polymerization at undesirable locations.

Numerous olefin monomers such as styrene, α-methyl styrene, acrylic acid and esters thereof, vinyl acetate, acrylonitrile, acrylamide, methacrylamide, etc. and such dienes (diolefins) as 1,3-butadiene, isoprene, and chloroprene, upon reaching refining devices during production and recovery, are exposed to certain conditions such as high temperature, high monomer concentration, coexistence of vapor and liquid phase, humidity, trace oxygen and iron rust which are highly conducive to the occurrence of popcorn polymerization. Fouling of equipment can even occur when unsaturated compounds in petroleum or its derivatives undesirably polymerize.

In the manufacturing of synthetic rubber and plastics for use by the military and others, the primary choice of feedstock is butadiene. Butadiene (BD) is a colorless gas at room temperature. Most of the supply of butadiene comes from olefin plants because butadiene is co-produced when other olefins are manufactured. Butadiene can be produced by catalytically dehydrogenating butane or butylene.

The dehydrogenating of butane or butylene to butadiene may be accomplished by passing the feed gas over a catalyst bed at 1200° F. (649° C.) and at reduced pressure. The effluent gas then passes through an extractive distillation process.

Although butadiene can be manufactured by catalytic dehydrogenation, most of the butadiene produced domestically is obtained by extractive distillation. Butadiene can be recovered and purified from $C_4$ streams by using a solvent that reduces the boiling point of the butadiene. The most popular solvents used to facilitate this extraction are N-methylpyrrolidone (NMP) and dimethylformamide (DMF).

The crude butadiene is further purified by distillation through a series of towers that separate residual solvent, C4 compounds, and other contaminants. A further component of the BD manufacturing process is the Recovery Solvent Section. From the stripper column, a slip stream of lean solvent is regenerated to remove heavies and contaminants. This reduces the presence of polymer loading and decomposition products.

During the purification steps of BD production, there are some undesirable BD polymerization reactions. Of these, the most unwanted is the formation of popcorn polymer. The effect of popcorn polymer on BD processing equipment is so severe that this material has actually been found to bend heat exchanger tubes.

Poly-butadiene can be produced commercially by way of an aqueous homopolymerization reaction. In order to actuate this polymerization process, hydrogen peroxide is used in excess of 7400 ppm to initiate butadiene to react to form poly-butadiene (Poly-BD). However, the presence of peroxides and trace levels of Poly-BD in the water from the decanter drum used in the process results in undesirable polymerization at the acetone column. Presently, Poly-BD manufacturers use sodium sulfite to control peroxide levels in the feed to the acetone drum, which feeds the acetone column, but this program is not very efficient in reducing peroxide levels. Also, other chemical suppliers have attempted to treat the polymerization problems with commercial antioxidants, but have experienced very little success. This failure can be linked directly to the economic limitations on inhibitor usage to control such relatively large concentrations of peroxides. This results in relatively small, but still significant amounts of hydrogen peroxide and other peroxides that are not destroyed, but which in turn results in undesired polymerization in the acetone column. Currently commercial Poly-BD producers can spend large sums annually on the use of sodium sulfite that is capable of removing only about 50% of the residual peroxides.

It would be desirable if a composition and method could be devised to inhibit the undesirable and unintentional polymerization of unsaturated (vinyl) monomers, particularly butadiene, but without having to require relatively large, and therefore costly, amounts of inhibitors.

SUMMARY OF THE INVENTION

Accordingly, it is an object of the present invention to provide a method and composition to effectively inhibit the polymerization of vinyl compounds, such as butadiene.

It is another object of the present invention to provide a method and composition to effectively inhibit the polymerization of olefins that is less expensive than using conventional antioxidant inhibitors because relatively less amount of the inhibitor is required to achieve acceptable polymerization inhibition.

Still another object of the invention is to permit use of a composition to effectively inhibit the polymerization of butadiene that uses readily available compounds.

In carrying out these and other objects of the invention, there is provided, in one form, a method for inhibiting the polymerization of unsaturated monomers that are polymerized by free radicals generated by peroxides, the method comprising adding to the unsaturated monomers an effective polymerization-inhibiting amount of an inhibitor selected from the group consisting of diamines, alkanolamines, and mixtures thereof.

DETAILED DESCRIPTION OF THE INVENTION

It has been discovered that the use of diamines and alkanolamines can effectively destroy hydrogen peroxide more efficiently than some commercially used inhibitors, such as sodium sulfite. It is believed that these classes of chemicals destroy hydrogen peroxide through one or more catalytic decomposition interactions, although it is not desired to limit the invention to any one particular theory or mechanism. Such compounds would include, but not be limited to, ethylenediamine (EDA) and monoethanolamine (MEA). These materials have been found to completely destroy hydrogen peroxide in a poly-butadiene sample obtained from a commercial Poly-BD producer in less than 30 minutes. A standard hydrogen peroxide test kit that can be purchased commercially was used to test for the effectiveness of these amines on peroxide destruction. The heat induced gum test, a standard test used to evaluate inhibitors in the petrochemical industry, was used herein to evaluate the effectiveness of these materials to inhibit polymerization of the Poly-BD sample.

It is expected that the polymerization inhibitors of this invention can be used in conjunction with any system that uses peroxides to generate free radicals for the intentional polymerization of a vinyl monomer, yet has trouble with trace amounts of the peroxide remaining in the system and causing polymerization at undesirable places and times. It is anticipated that the vinyl monomers with which the inhibitors of this invention may be used include, but are not necessarily limited to, styrene, α-methyl styrene, acrylic acid and esters thereof, vinyl acetate, acrylonitrile, acrylamide, methacrylamide, 1,3-butadiene, isoprene, chloroprene, and mixtures thereof. The monomer that is preferred to be inhibited against undesirable polymerization is 1,3-butadiene, or simply butadiene (BD).

The peroxides that may be treated and decomposed to prevent polymerization include, but are not necessarily limited to, hydrogen peroxide, alkyl peroxides, alkyloxy peroxides, aryl peroxides, aralkyl peroxides, and mixtures thereof.

The diamines useful as polymerization inhibitors in the compositions and methods of the invention have the structure:

$$X^1X^2NCH_2CH_2NY^1Y^2 \qquad (I)$$

where $X^1$, $X^2$, $Y^1$, and $Y^2$ are independently selected from the group consisting of hydrogen, straight or branched alkyl groups of 1 to 20 carbon atoms and alkylaryl groups of 1 to 20 carbon atoms. Preferably, the straight or branched alkyl groups have at least 2 carbon atoms and/or have up to 5 carbon atoms and the alkylaryl groups preferably have at least 2 carbon atoms and/or have up to 5 carbon atoms. Examples of suitable diamines include, but are not necessarily limited to, ethylenediamine, methylenediamine, propylenediamine, butylenediamine, dibutylethylenediamine, and mixtures thereof. A preferred diamine is ethylenediamine (EDA).

The alkanolamines useful in the methods and compositions of this invention have the structure:

$$X^1X^2NCH_2CH_2NOH \qquad (II)$$

where $X^1$ and $X^2$ are as defined above. Examples of suitable alkanolamines include, but are not necessarily limited to, monoethanolamine, ethyidiethanolamine, 2-amino-2-propanol, 3-amino-1,2-propanediol, 1-amino-2-propanol, and mixtures thereof. A preferred alkanolamine is monoethanolamine (MEA).

In one non-limiting embodiment of the invention, the process and compositions involve an absence of manganese (Mn) compounds.

Progrtions

A number of factors affect the effective amounts of the diamines and/or alkanolamines of this invention that would be useful to inhibit the polymerization of an unsaturated compound, including, but not necessarily limited to, the nature of the unsaturated compound, the concentration of the unsaturated compound, the nature and concentration of the peroxide, the temperature and pressure environment of the unsaturated compound, the nature of the particular diamine and/or alkanolamine used, and the like. These complex, interrelated factors make it difficult to specify in advance and/or with precision what effective proportions of the inhibitors should be in any given situation. Nevertheless, some general guidelines as to the effective proportion of the inhibitors in the unsaturated compound may be given.

The composition of this invention may have from about 1 to about 10,000 ppm of the inhibitor based on the total amount of unsaturated compound being treated. Preferably, the proportions are at least about 50, and may be less than about 500 ppm of the inhibitor, based on the total amount of unsaturated compound being treated.

The inhibitors may be simply mixed together into the unsaturated monomers to be inhibited. The inhibitors are not expected to work more advantageously at a particular temperature or pressure.

The invention will be further illustrated with respect to specific examples, which are not intended to limit the invention, but rather to more fully describe it.

Test Method

The samples for Examples 1–17 noted below were tested on the Decanter Effluent. The Decanter Effluent characteristics included 10,500 ppm $H_2O_2$ and 3.0 pH. The acetone feed was 7,500 ppm $H_2O_2$ and 4.8 pH.

TABLE A

Butadiene Polymerization Inhibition Using Diamines and Alkanolamines

| Ex. | Sample | Reaction (action) | Reactor time (min) | Peroxide (drops) | Dilution (ml/ml) | Peroxide (ppm) | Reduction % | pH | Treated Sample Appearance |
|---|---|---|---|---|---|---|---|---|---|
| 100% Dose | | | | | | | | | |
| 1 | Blank | — | 5 | 11 | 1/1000 | 10,500 | — | 3.0 | cloudy |
| 2 | 1S | slight vent | 30 | 2 | 1/1000 | 1,500 | 85.7 | 5.0 | cloudy, clear |
| 3 | 2M | slight vent | 33 | 5 | 1/200 | 950 | 91.0 | 10.3 | cloudy |

TABLE A-continued

Butadiene Polymerization Inhibition Using Diamines and Alkanolamines

| Ex. | Sample | Reaction (action) | Reactor time (min) | Peroxide (drops) | Dilution (ml/ml) | Peroxide (ppm) | Reduction % | pH | Treated Sample Appearance |
|---|---|---|---|---|---|---|---|---|---|
| 4 | 3E | good venting | 36 | 0 | * | 0 | 100.0 | 11.0 | cloudy |
| 5 | 4H | — | 53 | 4 | 1/1000 | 3,500 | 66.7 | 9.0 | cloudy |
| 6 | 5E | — | 43 | 0 | ∞ | 0 | 0.0 | 5.0 | cloudy, yellow |
| 7 | 6N | — | 45 | 11 | 1/1000 | 10,500 | 0.0 | 5.5 | cloudy, yellow |
| 50% Dose | | | | | | | | | |
| 8 | Blank | — | 139 | 10 | 1/1000 | 9,500 | — | 3.0 | |
| 9 | 1S | min. vent | 30 | 5 | 1/1000 | 4,500 | 52.6 | 5.0 | slightly clearer |
| 10 | 2M | min. vent | 27 | 10 | 1/250 | 2,375 | 75.0 | 9.5 | |
| 11 | 3E | good vent | 24/44 | 0 | 1/250, 1/30 | 0 | 100.0 | 10.0 | |
| 12 | 4H | — | 16 | 9 | 1/1000 | 8,500 | 10.5 | 9.0 | |
| 25% Dose | | | | | | | | | |
| 13 | 1S | — | 27 | 8 | 1/1000 | 7,500 | 21.1 | 5.0 | |
| 15 | 2M | min. vent | 26 | 3 | 1/1000 | 2,500 | 73.7 | 9.0 | sample fizzes w/ pH paper test |
| 16 | 3E | some vent | 25 | 0 | * | 0 | 100.0 | 9.5 | |
| 50 micromil | | | | | | | | | |
| 16 | 3E | — | 16 | 10 | 1/500 | 4,750 | 50.0 | 8.5 | |
| 17 | (7.0% dose) | — | 21 | 7 | 1/1000 | 6,500 | 31.6 | — | |

Legend:
1S = Sodium Sulfate (17%)
2M = MEA (concentrated)
3E = EDA (concentrated)
4H = Hydrazine (30%)
5E = Sodium Erythorbate (10%)
6N = Sodium Nitrate (15%)
*The EDA was either using up all of the peroxide or reacted with the molybdenum titrant. The sample turned very cloudy when the ammonia molybdate was added with no color changes after the sulfite pillow was added.
∞23 mils of 5E turned the sample yellow and the test kit didn't work well with this sample.

It may be seen from the results of Table A that MEA and EDA (Examples 3, 4, 10, 11, and 14–17) give the best polymerization reduction for each dosage level. As would be expected, the amount of polymerization reduction is reduced when the dosage is reduced. Nevertheless, EDA gave 100% reduction at the 100% (Ex. 4), 50% (Ex. 11) and 25% (Ex. 15) dosages. Even at the very small doses used in Examples 16 and 17 some polymerization reduction was noted. MEA also gave very good results.

In the foregoing specification, the invention has been described with reference to specific embodiments thereof, and has been demonstrated as effective in providing a composition for inhibition of polymerization of unsaturated compounds, such as butadiene. However, it will be evident that various modifications and changes can be made thereto without departing from the broader spirit or scope of the invention as set forth in the appended claims. Accordingly, the specification is to be regarded in an illustrative rather than a restrictive sense. For example, specific diamines or alkanolamines, other than those specifically tried, in other proportions or ratios or added in different ways, falling within the claimed parameters, but not specifically identified or tried in a particular composition to improve the polymerization inhibition herein, are anticipated to be within the scope of this invention.

I claim:

1. A method for inhibiting a polymerization of unsaturated monomers that are polymerized by free radicals generated by peroxides, the method comprising adding to the unsaturated monomers a polymerization-inhibiting amount of an inhibitor selected from the group consisting of diamines, alkanolamines, and mixtures thereof.

2. The method of claim 1 where the unsaturated monomer is selected from the group consisting of styrene, α-methyl styrene, acrylic acid and esters thereof, vinyl acetate, acrylonitrile, acrylamide, methacrylamide, 1,3-butadiene, isoprene, chloroprene and mixtures thereof.

3. The method of claim 1 where the unsaturated monomer is 1,3-butadiene.

4. The method of claim 1 where the diamines have the structure:

$$X^1X^2NCH_2CH_2NY^1Y^2$$

where $X^1$, $X^2$, $Y^1$, and $Y^2$ are independently selected from the group consisting of hydrogen, straight or branched alkyl groups of 1 to 20 carbon atoms and alkylaryl groups of 1 to 20 carbon atoms, and where the alkanolamines have the structure:

$$X^1X^2NCH_2CH_2NOH$$

where $X^1$ and $X^2$ are as defined above.

5. The method of claim 1 where the diamine is ethylenediamine and the alkanolamine is monoethanolamine.

6. The method of claim 1 where the inhibitor is present in an amount ranging from about 1 to about 10,000 ppm based on the amount of unsaturated monomer present.

7. The method of claim 1 where the peroxide is hydrogen peroxide.

8. A method for inhibiting a polymerization of unsaturated monomers that are polymerized by free radicals generated by peroxides, the method comprising of an inhibitor selected from the group consisting of diamines, alkanolamines, and mixtures thereof, where the unsaturated monomer is selected from the group consisting of styrene, α-methyl styrene, acrylic acid and esters thereof, vinyl acetate, acrylonitrie, acrylamide, methaclrylamide, 1,3-butadiene, isoprene, chloroprene and mixtures thereof, where the diamines have the structure:

$X^1X^2NCH_2CH_2NY^1Y^2$ where $X^1$, $X^2$, $Y^1$, and $Y^2$ are independently selected from the group consisting of hydrogen, straight or branched alkyl groups of 1 to 20 carbon atoms and aalkylaryl groups of 1 to 20 carbon atoms; and where the alkanolamines have the structure:

$X^1X^2NCH_2CH_2NOH$ where $X^1$ and $X^2$ are as defined above.

9. The method of claim 8 where the unsaturated monomer is 1,3-butadiene.

10. The method of claim 8 where the diamine is ethylenediamine and the alkanolamine is monoethanolamine.

11. The method of claim 8 where the inhibitor is present in an amount ranging from about 1 to about 10,000 ppm based on the amount of unsaturated monomer present.

12. The method of claim 8 where the peroxide is hydrogen peroxide.

13. The method of claim 8 where the peroxide is catalytically destroyed by the inhibitor.

* * * * *